United States Patent [19]

Lonardo

[11] E Patent Number: Re. 33,762

[45] Reissued Date of Patent: Dec. 10, 1991

[54] THERAPEUTIC LEG AND FOOT DEVICE

[75] Inventor: Robert Lonardo, Treasure Island, Fla.

[73] Assignee: L'Nard Associates, Inc., St. Petersburg, Fla.

[21] Appl. No.: 578,592

[22] Filed: Sep. 4, 1990

Related U.S. Patent Documents

Reissue of:

[64] Patent No.: 3,976,059
Issued: Aug. 24, 1976
Appl. No.: 584,371
Filed: Jun. 6, 1975

U.S. Applications:

[63] Continuation of Ser. No. 399,365, Sep. 21, 1973, which is a continuation-in-part of Ser. No. 237,643, Mar. 24, 1972, abandoned, which is a continuation-in-part of Ser. No. 86,547, Nov. 3, 1970, abandoned.

[51] Int. Cl.[5] ..... A61F 3/00

[52] U.S. Cl. ..... 128/80 E; 128/166; 128/87 R; 128/89 R

[58] Field of Search ..... 128/80 R, 80 D, 80 DB, 128/80 E, 80 G, 80 H, 80 J, 25 R, 25 B, 83, 83.5, 84 R, 85, 87 R, 89 R, 90, 165, 166

[56] References Cited

U.S. PATENT DOCUMENTS

| | | | |
|---|---|---|---|
| Re. 27,957 | 4/1974 | Larson | 128/89 R |
| 114,669 | 5/1871 | Grant | 128/80 J |
| 433,227 | 7/1890 | Beacock | 128/90 |
| 1,334,596 | 3/1920 | Crouch | 128/85 |
| 1,656,322 | 1/1928 | Fischer | 128/80 J |
| 1,948,534 | 2/1934 | Nelson et al. | 128/25 B |
| 2,492,920 | 12/1949 | Koster | 128/80 R |
| 2,523,606 | 8/1950 | Young | 128/87 R X |
| 2,847,991 | 8/1958 | Andrews | 128/80 E |
| 2,911,657 | 11/1959 | Streeter | 128/149 UX |
| 2,986,747 | 6/1961 | Posey | 128/80 E |
| 3,086,522 | 4/1963 | Frohmader | 128/80 J |
| 3,171,407 | 3/1965 | Rogus | 128/80 J |
| 3,304,937 | 2/1967 | Callender, Jr. | 128/80 R |
| 3,523,526 | 8/1970 | Phelps | 128/80 R |
| 3,557,782 | 1/1971 | Wafer | 128/80 R |
| 3,584,622 | 6/1971 | Domenico | 128/166 |
| 3,589,359 | 6/1971 | Hill | 128/80 E |
| 3,606,884 | 9/1971 | Peter | 128/80 R |
| 3,618,946 | 11/1971 | Lee | 128/80 R X |
| 3,698,389 | 10/1972 | Guedel | 128/77 |
| 3,779,654 | 12/1973 | Horne | 128/80 H X |

FOREIGN PATENT DOCUMENTS

| | | | |
|---|---|---|---|
| 937846 | 1/1956 | Fed. Rep. of Germany | 128/80 E |
| 698294 | 10/1953 | United Kingdom | 128/87 A |

OTHER PUBLICATIONS

DePuy Fracture Appliances Catalogue, p. 101, DePuy Combination Leg Splint, & Buck's Extension Leg Splint.

*Primary Examiner*—Richard J. Apley
*Assistant Examiner*—Linda C. M. Dvorak
*Attorney, Agent, or Firm*—Zarley, McKee, Thomte, Voorhees & Sease

[57] ABSTRACT

A therapeutic leg and foot device comprising an L-shaped member having an elongated channel-like portion adapted to fit the posterior region of the lower leg and a foot portion extending integrally at right angles therefrom. The integral connection is curved to avoid contact with the patient's heel when the device is in place. The channel shape flattens out at the curved portion and is narrowed to promote the required flexing at this point. The device is constructed of resilient transparent acrylic plastic material which is resilient under a stress load but has sufficient rigidity to maintain a bed patient's foot in properly disposed position to prevent bed sores or drop foot. However, when used in the correction of drop foot, the foot portion is flexed away from the perpendicular to an obtuse angle with the leg portion to conform to the deformity. In this position the device exerts a 30 to 50 lb. pressure on the foot area to bias the foot back into normal position. There is also an equal amount of pressure or counter force on the lateral arch to correct outward turning of a foot usually associated with a foot drop deformity. This rigid flexibility also permits its use as an ambulation aid in gait training. The device is provided with releasable mans for securing to the patient's foot. Attachments may be made for preventing undesirable rotation of the leg; for making the device rigid to maintain the immobility of the foot and heel; and for maintaining the bed sheets and blankets in spaced relation to the patient's toes.

10 Claims, 2 Drawing Sheets

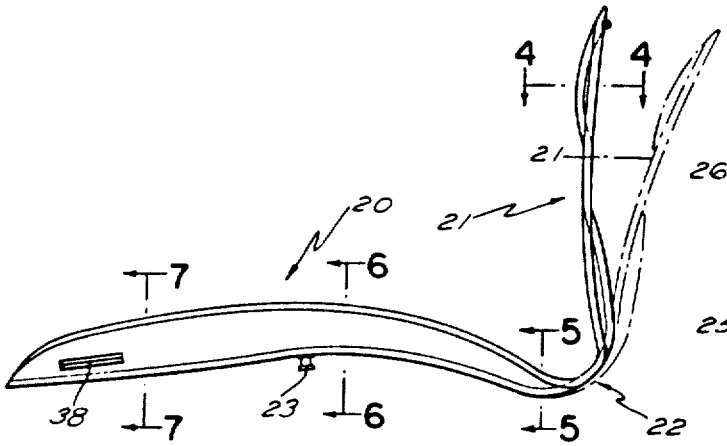
FIG. 1
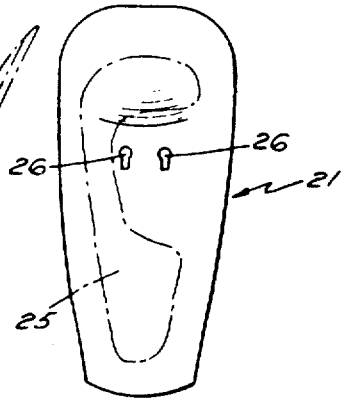
FIG. 2
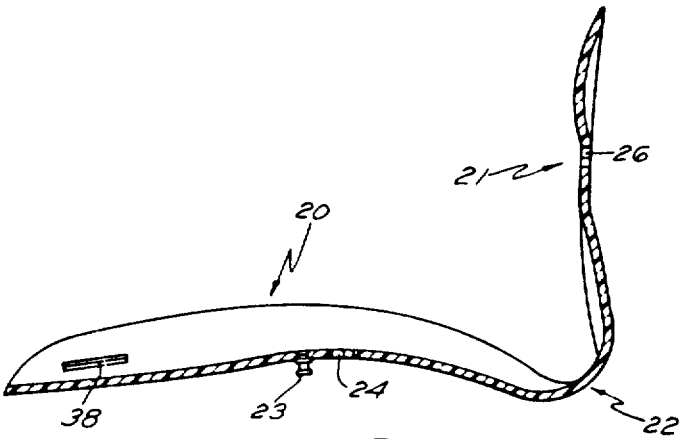
FIG. 3
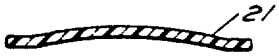
FIG. 4
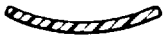
FIG. 5
FIG. 6
FIG. 7
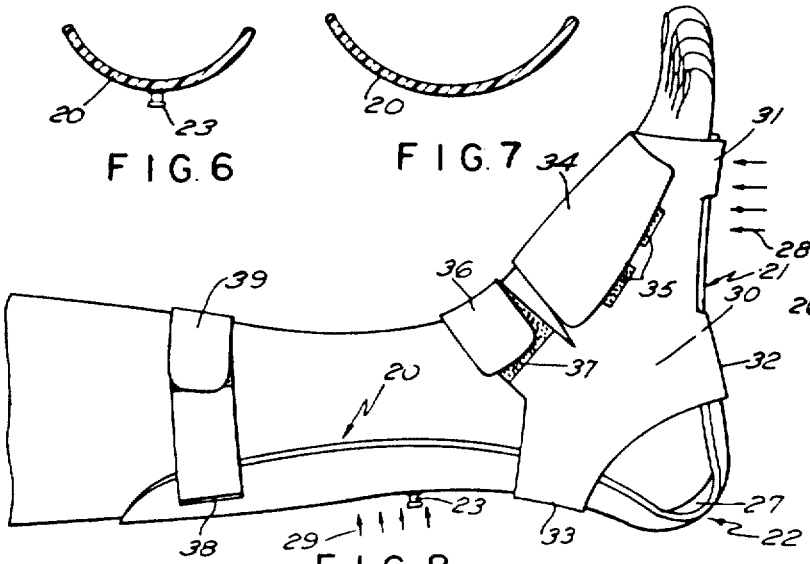
FIG. 8
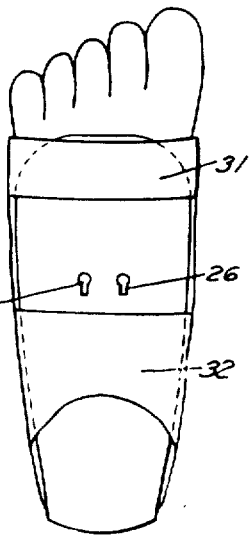
FIG. 9

THERAPEUTIC LEG AND FOOT DEVICE

Matter enclosed in heavy brackets [ ] appears in the original patent but forms no part of this reissue specification; matter printed in italics indicates the additions made by reissue.

BACKGROUND OF THE INVENTION

This application is a [substitute] *continuation* [for] *of* my *co-pending* application Ser. No. 399,365, filed 9/21/73, which was a continuation-in-part, all under the same title, of [a co-pending] application Ser. No. 237,643, filed Mar. 24, 1972, now [both] abandoned and entitled THERAPEUTIC LEG AND FOOT DEVICE *which was a continuation-in-part of my application Ser. No. 86,547 filed 11/3/70, now abandoned.*

Therapeutic devices for preventing drop foot, maintaining the patient's foot in proper position, and for acting as a heel guard are well known in the art. For example, U.S. Pat. No. 3,345,654 illustrates a typical construction of such a device.

However, these devices are merely splints and are not primarily designed to correct an existing condition. They are not designed to apply a corrective pressure to the foot. As a matter of fact, their rigidity precludes their use to correct an existing condition.

Furthermore, they are not designed to act as a walking brace or ambulation aid in gait training. This is important where the patient has been bed ridden for an extended period. This is especially true where the foot and leg have been held rigid.

SUMMARY OF THE INVENTION

The device of the present invention is truly therapeutic device and not a mere leg brace or splint. It is designed to provide a steady and accurately placed pressure on the sole and calf to correct existing deformities of the foot. Provision is made for augmenting the pressure, if necessary. When in place, the device can be worn inside of the shoe and act as an ambulation aid. This it does by applying an active corrective pressure under normal walking conditions and flexing with the movement of the toes and heel as in natural walking. All this while the pressure is applied to the first, third, fourth and fifth metatarsal bones and arch, to bring the foot automatically upward.

The device is also highly versatile. It can be made rigid by the addition of an easily mounted attachment for the purpose of holding the foot or heel in a rigid position. Another attachment will prevent rotation of the patient's foot, leg or hip. This may be necessary in a post operative condition.

A further attachment keeps sheets and blankets away from the patient's toes and foot while lying in bed. And finally, the device is made to receive any other suitable attachment such as a spreader for retaining the legs in spread position.

It should be noted that in the case of medical or surgical work on the heel and adjacent areas, the device will retain the foot in fixed position while maintaining a spaced relation with the heel. This permits light bandaging, makes it easily accessible to the doctor for examination, and eliminates the need for immobilizing heavy bandages or casts.

DESCRIPTION OF THE DRAWINGS

In the drawings:

FIG. 1 is a side elevation of the device of the present invention showing its flexing position and dynamic return;

FIG. 2 is a longitudinal section thereof;

FIG. 3 is an end view showing the area for the proper application of corrective pressure;

FIG. 4 is a section taken on line 4—4 on FIG. 1;

FIG. 5 is a section taken on line 5—5 on FIG. 1;

FIG. 6 is a section taken on line 6—6 on FIG. 1;

FIG. 7 is a section taken on line 7—7 on FIG. 1;

FIG. 8 is a view similar to FIG. 1 with the device mounted on a patient in a prone position;

FIG. 9 is an end view similar to FIG. 3 with the device mounted as shown in FIG. 8;

DESCRIPTION OF THE INVENTION

Figure 10:
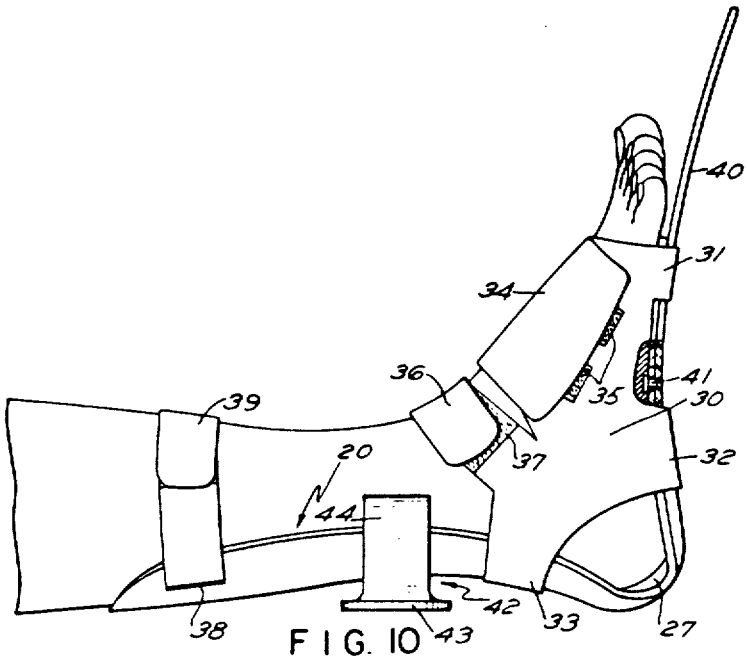
FIG. 10 is a view similar to FIG. 8 showing the mounting of several attachments.

Referring to the drawings in more detail, the device of the present invention is more clearly illustrated in FIGS. 1 to 7, inclusive. The device is molded of an acrylic transparent thermo-plastic material in a general L-shape, forming a leg portion 20 and a foot portion 21 extending integrally from a curved heel section 22 at right angles to the leg portion 20.

The leg portion 20 is contoured and channeled, as shown in FIGS. 1, 3, 6 and 7, so as to comfortably receive the posterior region of the lower leg. It is specifically depressed just above the ankle bone, see FIG. 8, and below the greater calf to act as a support and receive most of the weight concentration This is the area that supplies the counter-force for the flexing pressure of the foot portion 21 as hereinafter described. The portion 20 is provided at this point with a central stud 23 and a pair of spaced keyhole slots 24 adjacent the stud 23 toward the heel end.

The foot portion 21 is also contoured and channeled but to a lesser degree, see FIGS. 1, 2 and 4. The length of the portion 21 is such that its upper end terminates well short of the patient's toes when worn as in FIGS. 8 and 9. The device is flexible, and when the foot portion 21 is pulled into the dotted line position shown in FIG. 1, it will apply pressure to the bottom of the heel, the lateral arch, and the transverse metatarsal bones and arch as shown in the broken line area 25 in FIG. 2. The central portion of the foot portion 21 is also provided with a pair of keyhole slots 26, see FIGS. 2 and 9.

To permit a proper flexing action, the heel portion 22 is provided with an area of the least amount of contouring and channeling, being almost flat, see FIGS. 3 and 5. The curvature is such that not only is there no pressure applied to the rear of the patient's heel, but there is an actual space 27 between the patient's heel and the heel portion 22 when the device is in place as in FIGS. 8 and 9.

Since the most important function of the device is its ability to flex at 22 to apply the proper therapeutic pressure, the material and construction at this point is of prime importance. First of all, rigidity along the portion 20 is supplied in part by its channel shape. This channeling gradually disappears as the heel portion 22 is reached. FIG. 7 shows the largest and deepest channeling, FIG. 6 is smaller, and FIG. 5, closet to the portion 22, shows it virtually gone. At the point 22, the device should be substantially (possibly not completely) flat. Furthermore, as can be seen in FIGS. 5, 6 and 7, the device is narrowest at this point the degree of flexibility can thus be controlled by the degree of channeling and the narrowing of the material at the heel.

Since flexibility is essential, the material is also important. The device is made of an acrylic thermo-plastic material approximately 0.125 inch in thickness. In small sizes for children, it may be only 0.087 inch thick. The leg portion 20 is approximately 10 inches long and the foot portion 21 is approximately 6 inches long. The heel portion 22 is approximately 1½ inches across. To complete the construction, the leg portion 20 is approximately 4 inches at its maximum width, the foot portion 21 3¾ inches, and the heel portion 22 only 2 inches wide.

With the above construction, the device will apply a pressure of 30 to 50 lbs. when flexed. Applicant has found that the acrylic plastic has the required characteristics. However, the constant flexing and use under stress loads requires fatigue strength, longevity, and resiliency under the stress loads over long periods of time. The acrylic filling these requirements is called "Nyloplex" and is sold by Fillauer Surgical Supplies of Chattanooga, Tenn. A product called "Lexan" manufactured by General Electric Cimpany is also satisfactory but slightly more sluggish in its flexing reaction. As with most acrylics, the above products have a "memory" so that they return to their original right angled form after each flexing.

The device is light in weight, approximately 6 oz., but the flexible acrylic has a tensile strength to withstand up to 250 lbs. of continuous resistance without fracturing, losing shape, or distorting. When flexed into the dotted line position shown in FIG. 1, it will exert a force of 30 to 50 lbs. pressure to the area shown by the arrows 28 in FIG. 8. The pressure is applied against the counter-pressure at the calf shown by the arrows 29.

This is the action necessary to correct a foot deformity such as drop foot. The patient's foot is placed into the device by flexing the foot portion 21 to an angle, FIG. 1, which will permit the insertion of the foot, then the portion 21 is released to apply the pressure. Any suitable means may be used to secure the device to the leg and foot of the patient. For example, viewing FIGS. 8 and 9, I use a soft leather sleeve or sandal 30 which is slipped over the patient's foot and the foot portion 21 of the device. It is provided with a cut out heel portion with strips 31 and 32 passing under the foot and strips 33 behind the upper heel. The front is provided with a flap 34 having any suitable fastening means such as the Velcro fastener 35, for securement around the instep. An additional strip 36, provided with a Velcro fastener 37, extends above the ankle region. In addition to the sandal 30, the leg portion 20 is provided with slots 38 adjacent the rear upper end. A strip 39 extends around the leg through the slots 38 to complete the mounting of the device.

With the device worn as shown in FIGS. 8 and 9, the application of the pressure as illustrated by the flexing action in FIG. 1 and the arrows 28 in FIG. 8 will correct any drop foot or similar deformity and will certainly prevent the formation thereof. Furthermore, the counter force pressure on the lateral arch will correct any outward turning of the foot usually associated with a foot drop deformity. The device is comfortable and will be tolerated by the patient over extended periods of time. It eliminates the need for weighted bags, foot boards, pillows, heavy dressings, and many other ineffective methods of treatment. Note that the device is always in place, whereas the other methods are hit or miss depending on the position of the patient. The device will accommodate either the right or left foot, male or female, and may be reused on another patient.

The device is also designed to be used in the prevention of heel decubitus and aid in the heeling of an existing one. Since the heel is suspended at 27 it clears the tender area and there is no contact or pressure. The transparency of the device allows the involved area to be constantly observed. In surgery, the device holds the foot rigid and allows the use of a light bandage for frequent observation by the doctor during healing.

When the device is in use, it may also be found necessary to keep the sheets and blankets off the patient's toes. To this end I provide the attachment shown in FIGS. 10 and 11. An elongated strap-like member 40 is curved to conform to the contour of the foot portion 21. It is provided with a pair of studs 41 adjacent the lower end. The member 40 is slipped under the strip portion 31 of the member 30, the studs 41 locking in the slots 26. The member 40 thus extends above the toes and keeps the sheets and blankets at a distance.

Figure 11:
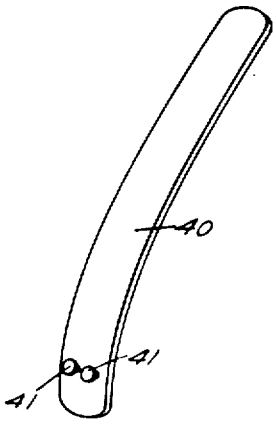
FIG. 11 is a perspective view of the attachment for maintaining the bed sheet and blanket spaced from the toes.
Figure 12:
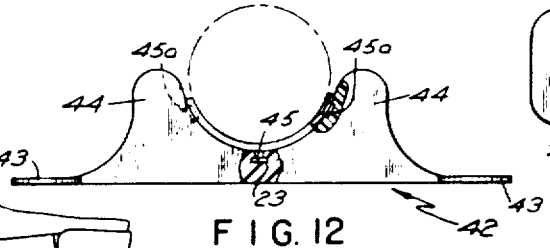
FIG. 12 is a front view of the attachment for preventing rotation.
Figure 13:
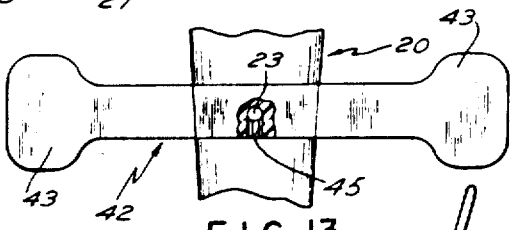
FIG. 13 is a bottom view of the attachment shown in FIG. 12, partially broken away.

It is often desirable to provide means for preventing rotation of the patient's leg for hip or leg conditionsa and for providing immobility after operations in these areas. This is accomplished by the attachment shown in FIGS. 10, 12 and 13. An elongated plastic member 42 is provided with a flat bottom and enlarged ends 43. The center is provided with a cradle portion 44 adapted to receive the leg and leg portion 20 (broken lines in FIG. 12). The leg portion 20 is locked to the member 42 by providing the cradle portion 44 with a central keyhole slot 45 for receiving the stud 23. For additional immobility, the parts may be provided at each side with snap fasteners **45*a* on the cradle portion 44 and leg portion 20. As can be seen in FIGS. 10 and 12, the attachment 42 prevents rotation of the patient's leg in the device. Note that this attachment can be used simultaneously with the attachment 40 as shown in FIG. 10**.

While the construction is designed to provide a flexing pressure of 30 to 50 lbs., in certain extreme conditions it may be desirable to increase the pressure by an additional 20 to 25 lbs. In such cases the attachment shown in FIG. 14 may be used. This comprises an L-shaped strip 46 of the same flexible acrylic material as the device itself. It is shaped to the outer contour of the device, having a leg portion 47, heel 48, and a foot portion 49. The foot portion 49 extends upwardly beyond the toes to perform the function of the attachment 40 to space the sheets and blankets from the toes. The strip 46 is provided with a keyhole slot for receiving the stud 23 of the leg portion 20 and is provided with studs 50 for attachment to the keyhole slots 26 in the foot portion 21. In the mounted position shown in FIG. 14, the strip 46 adds 20 to 25 lbs. to the flexed pressure of the foot portion 21.

Figure 14:
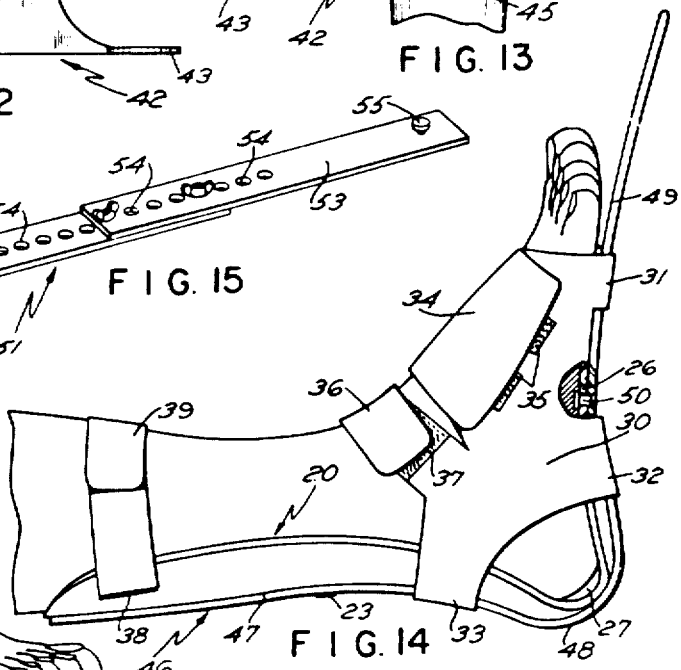
FIG. 14 is a view similar to FIGS. 8 and 10 showing the addition of still another attachment.

In certain surgical applications it may become necessary to retain the foot in a rigid, immovable position such as shown in FIG. 14. In such cases, the attachment 46 is made of a rigid material such as a metal or rigid plastic without flexibility. Its construction and method of mounting would be the same as the member 46, but it would hold the foot rigidly by counteracting the flexibility of the main device.

Figure 15:
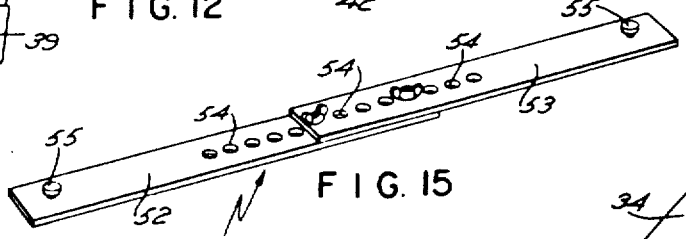
FIG. 15 is a perspective view of the spreading attachment.

Another useful attachment for the device is the spreader 51 shown in FIG. 15. In surgical procedures involving thighs, groin and related areas, it may be necessary to keep the patient's legs spread during healing. In such cases a device of the present invention is first mounted on each foot and leg. The spreader 51 comprises a pair of strips 52 and 53 adjustably connected at 54. At their outer ends, the strips 52 and 53 are provided with studs 55 which can be mounted in the keyhole slots 24 on the leg portions 20 to spread the legs apart. Alternatively, the spreader 51 can be mounted on the foot sections 21 by attaching the studs 55 to the keyhole slots 26. Either method will result in the same spread position.

Figure 16:
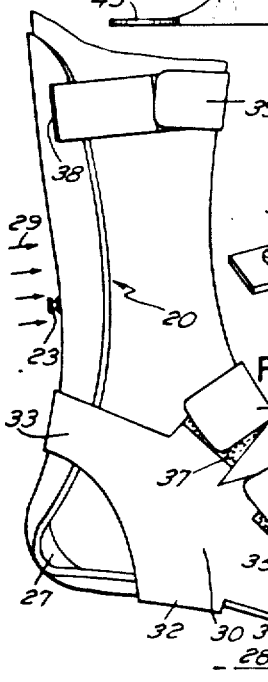
FIG. 16 is a side elevation illustrating the use of the device as an ambulation aid in an existing contracture deformity.

As stated hereinabove, one of the advantages of the present invention is its use as an ambulation aid in gait training. As can be seen in FIG. 16, the application of pressures at the points 28 and 29 is of prime importance when walking. Thus the inherent flexibility of the device will tend to force the foot into a proper walking action including the flexing of the foot and lifting to move into forward position. The device will apply the same pressure action while walking as it does to correct an abnormality in the prone position shown in FIG. 8. It should be noted that the fact that the foot section 21 is short of the toes permits natural movement of the toes and feet while walking. This also permits the patient's own shoe to be worn directly over the device without the discomfort. The device thus acts as a walking brace and the pressure on the foot at 28 ensures a proper walking step without dragging, regardless of the corrections being made to the foot position.

The present invention therefore provides a therapeutic leg and foot device of simple construction and designed for its intended purpose. However, the device is extremely versatile in use. It can be used in a prone or in an ambulating position, and it can be used with its attachments to alleviate, correct, or prevent various conditions.

Other advantages of the present invention will be readily apparent to a person skilled in the art.

I claim:

1. A therapeutic leg and foot device comprising an L-shaped member of a flexible, transparent, acrylic, plastic, said member having a generally contoured and channel-shaped leg portion, a curved heel portion integral with one end of said leg portion, and a generally contoured foot portion extending integrally from said heel portion at right angles to said leg portion, said foot portion being shorter than the adult human foot, the channel shape of said leg portion being substantially flattened at said heel portion, said curved heel portion being narrower than said foot and leg portions and having a free and unflanged edge to permit flexing of said foot portion with respect to said leg portion, said foot portion exerting a pressure of 30 to 50 lbs. toward said leg portion when said foot portion is flexed away from the right angle position, and means for releasably securing the device to the leg and foot of a patient.

2. A device as in claim 1, wherein said heel portion is curved away from the patient's heel to provide a space therebetween, and wherein the pressure of said foot portion is applied against the heel, lateral arch and transverse metatarsal arch portions of the foot.

3. A device as in claim 1, wherein said device is provided with an attachment for maintaining the bed sheets and blankets in spaced relation to the patient's toes, said attachment comprising an elongated strip of rigid material and means mounting one end of said strip to said foot portion, said strip extending upwardly above the patient's toes.

4. The device as in claim 1, wherein said device is provided with an attachment for preventing rotation of the leg, said attachment comprising an elongated plastic member having a flat bottom and enlarged ends, said member having an arcuate cradle portion for receiving said leg portion therein, and means immovably releasably locking said leg portion in said cradle portion.

5. A device as in claim 1, wherein said device is provided with an attachment for adding 20 to 25 lbs. flexing pressure to said foot portion, said attachment comprising an L-shaped strip of flexible acrylic plastic material adapted to extend along the outer surface of said device, and means releasably attaching said strip to said device.

6. A device as in claim 1, wherein said device is provided with an attachment for making the device rigid and in inflexible, said attachment comprising an L-shaped strip of rigid material adapted to extend along the outer surface of said device, and means releasably attaching said strip to said device.

7. A device as in claim 5, wherein said strip is elongated to extend above the toes to keep the sheets and blankets away from the toes.

8. A device as in claim 6, wherein said strip is elongated to extend above the toes to keep the sheets and blankets away from the toes.

9. A device as in claim 2, wherein said device is provided with an attachment for maintaining the bed sheets and blankets in spaced relation to the patient's toes, said attachment comprising an elongated strip of rigid material and means for mounting one end of said strip to said foot portion, said strip extending upwardly above the patient's toes.

10. A device as in claim 4, wherein said heel portion is curved away from the patient's heel to provide a space therebetween, and wherein the pressure of said foot portion is applied against the heel, lateral arch, and transverse metatarsal arch portions of the foot.

* * * * *